United States Patent
Liu

(10) Patent No.: US 10,459,072 B2
(45) Date of Patent: Oct. 29, 2019

(54) ULTRASOUND PROBE AND ULTRASOUND SYSTEM

(71) Applicants: QISDA OPTRONICS (SUZHOU) CO., LTD., Suzhou, Jiangsu Province (CN); QISDA CORPORATION, Taoyuan (TW)

(72) Inventor: Jian-Hung Liu, New Taipei (TW)

(73) Assignees: Qisda (Suzhou) Co., Ltd., Suzhou (CN); Qisda Corporation, Taoyuan (TW)

( * ) Notice: Subject to any disclaimer, the term of this patent is extended or adjusted under 35 U.S.C. 154(b) by 299 days.

(21) Appl. No.: 15/379,510

(22) Filed: Dec. 15, 2016

(65) Prior Publication Data
US 2017/0343657 A1    Nov. 30, 2017

(30) Foreign Application Priority Data

May 27, 2016 (CN) ............................ 2016 1 0363265

(51) Int. Cl.
*G01S 7/52* (2006.01)
*A61B 8/14* (2006.01)
*A61B 8/00* (2006.01)
*G01N 29/04* (2006.01)
*G01S 15/89* (2006.01)
*G01N 29/22* (2006.01)
*G01N 29/34* (2006.01)

(52) U.S. Cl.
CPC ............ *G01S 7/52079* (2013.01); *A61B 8/14* (2013.01); *A61B 8/4281* (2013.01); *A61B 8/4444* (2013.01); *A61B 8/4483* (2013.01); *G01N 29/043* (2013.01); *G01N 29/221* (2013.01); *G01N 29/348* (2013.01); *G01S 7/5202* (2013.01); *G01S 7/52022* (2013.01); *G01S 7/52042* (2013.01); *G01S 15/8913* (2013.01); *G01S 15/8915* (2013.01); *G01S 15/8952* (2013.01); *G01N 2291/104* (2013.01)

(58) Field of Classification Search
CPC ..... G01S 7/52079; A61B 8/14; A61B 8/4281; A61B 8/4444
USPC ......................................................... 73/628
See application file for complete search history.

(56) References Cited

U.S. PATENT DOCUMENTS 3,712,119 A    1/1973  Cross
3,987,673 A   10/1976  Hansen
(Continued)

FOREIGN PATENT DOCUMENTS

CN    104549978 A    4/2015
JP   2009296055 A   12/2009
TW    201512655 A    4/2015

*Primary Examiner* — Tarun Sinha

(57) ABSTRACT

An ultrasound probe includes a casing, a first transmitting unit, a second transmitting unit and a receiving unit. The first transmitting unit is used for transmitting a first push beam and the first push beam has a first transmitting frequency. The second transmitting unit is used for transmitting a second push beam and the second push beam has a second transmitting frequency. The receiving unit has a receiving frequency and is used for selectively receiving a reflective wave of the first push beam and the second push beam, wherein the receiving frequency is covered with the first transmitting frequency and the second transmitting frequency. The receiving unit, the first transmitting unit and the second transmitting unit are disposed in the casing side by side.

14 Claims, 1 Drawing Sheet

(56) References Cited

U.S. PATENT DOCUMENTS

| | | | |
|---|---|---|---|
| 5,460,595 A | 10/1995 | Hall | |
| 2002/0050169 A1* | 5/2002 | Ritter | G01S 7/52046 73/606 |
| 2011/0184287 A1* | 7/2011 | McAleavey | A61B 8/4483 600/438 |
| 2012/0232397 A1* | 9/2012 | Ohshima | A61B 8/4472 600/447 |
| 2013/0123630 A1* | 5/2013 | Freiburger | G01S 7/52042 600/443 |
| 2013/0241356 A1* | 9/2013 | Kim | A61B 8/4444 310/336 |
| 2015/0289846 A1* | 10/2015 | Park | A61B 8/5207 600/447 |

* cited by examiner

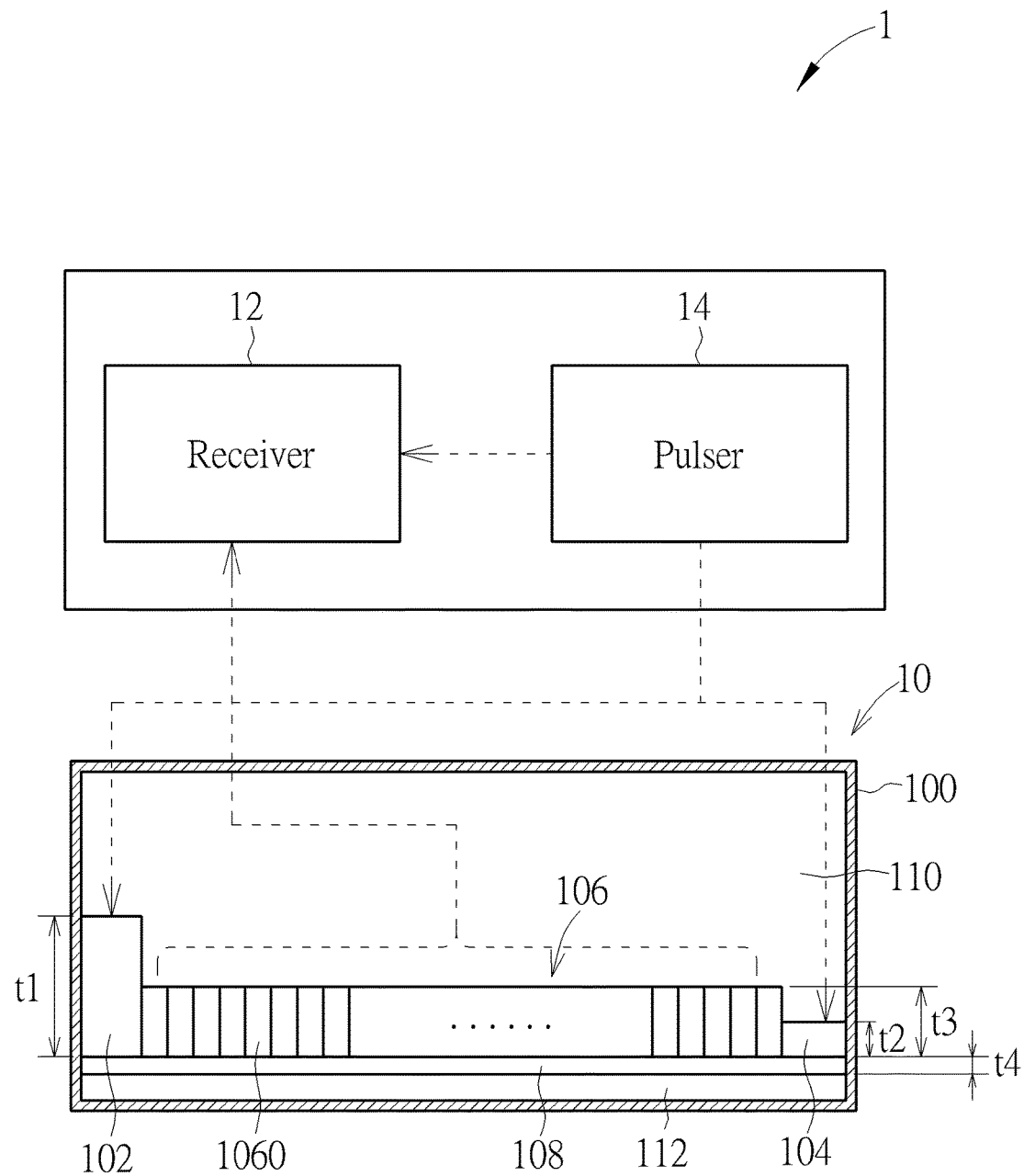

ULTRASOUND PROBE AND ULTRASOUND SYSTEM

CROSS REFERENCE TO RELATED APPLICATION

This application claims the benefit of China Application No. 201610363265.7, which was filed on May 27, 2016, and is incorporated herein by reference.

BACKGROUND OF THE INVENTION

1. Field of the Invention

The invention relates to an ultrasound probe and an ultrasound system and, more particularly, to an ultrasound probe and an ultrasound system capable of transmitting two push beams with different frequencies.

2. Description of the Prior Art

Since ultrasound scanning equipments do not destroy material structure and cell, ultrasound scanning equipments are in widespread use for the field of material and clinical diagnosis. When an ultrasound probe is scanning, the ultrasound probe transmits a push beam with a specific intensity to a tissue, so as to vibrate the tissue. Then, the vibration spreads in all directions with a specific speed based on a characteristic of the tissue, wherein a reflective wave perpendicular to a direction of the push beam is called "shear wave". Since a wave speed of the shear wave changes with the hardness of the tissue, the hardening of the tissue can be obtained by measuring the wave speed of the shear wave. In general, a shear wave generated by a push beam with low frequency may spread with a long distance, but the resolution is bad. Therefore, the push beam with low frequency is suitable for scanning a tissue of liver, breast or the like. Furthermore, a shear wave generated by a push beam with high frequency may spread with a short distance, but the resolution is good. Therefore, the push beam with high frequency is suitable for scanning a tissue of a small area. In the prior art, the ultrasound probe can only transmit a push beam with one single frequency. When a doctor wants to perform the ultrasound scanning for tissues located at different distances, he/she has to change different ultrasound probes and it is very inconvenient in use.

SUMMARY OF THE INVENTION

An objective of the invention is to provide an ultrasound probe and an ultrasound system capable of transmitting two push beams with different frequencies, so as to solve the aforesaid problems.

According to an embodiment of the invention, an ultrasound probe comprises a casing, a first transmitting unit, a second transmitting unit and a receiving unit. The first transmitting unit is used for transmitting a first push beam and the first push beam has a first transmitting frequency. The second transmitting unit is used for transmitting a second push beam and the second push beam has a second transmitting frequency. The receiving unit has a receiving frequency and the receiving unit is used for selectively receiving a reflective wave of the first push beam and the second push beam, wherein the receiving frequency is covered with the first transmitting frequency and the second transmitting frequency. The receiving unit, the first transmitting unit and the second transmitting unit are disposed in the casing side by side.

According to another embodiment of the invention, an ultrasound system comprises an ultrasound probe, a receiver and a pulser. The ultrasound probe comprises a casing, a first transmitting unit, a second transmitting unit and a receiving unit. The first transmitting unit is used for transmitting a first push beam and the first push beam has a first transmitting frequency. The second transmitting unit is used for transmitting a second push beam and the second push beam has a second transmitting frequency. The receiving unit has a receiving frequency, wherein the receiving frequency is covered with the first transmitting frequency and the second transmitting frequency. The receiving unit, the first transmitting unit and the second transmitting unit are disposed in the casing side by side. The receiver is electrically connected to the receiving unit. The pulser is electrically connected to the first transmitting unit, the second transmitting unit and the receiver. The pulser is used for triggering the first transmitting unit and the second transmitting unit to selectively transmit the first push beam and the second push beam.

As mentioned in the above, the invention integrates the two transmitting units and the receiving unit into the ultrasound probe, wherein the two transmitting units can transmit two push beams with different frequencies. Accordingly, the ultrasound probe of the invention can selectively transmit a push beam with low frequency to scan a tissue of liver, breast or the like or transmit a push beam with high frequency to scan a tissue of a small area. In other words, the ultrasound probe of the invention can perform ultrasound scanning for tissues located at different distances. Therefore, the invention is very convenient in use.

These and other objectives of the present invention will no doubt become obvious to those of ordinary skill in the art after reading the following detailed description of the preferred embodiment that is illustrated in the FIGURE.

BRIEF DESCRIPTION OF THE DRAWINGS

The FIGURE is a schematic diagram illustrating an ultrasound system according to an embodiment of the invention.

DETAILED DESCRIPTION

Referring to the FIGURE, the FIGURE is a schematic diagram illustrating an ultrasound system 1 according to an embodiment of the invention. As shown in the FIGURE, the ultrasound system 1 comprises an ultrasound probe 10, a receiver 12 and a pulser 14. The ultrasound probe 10 comprises a casing 100, a first transmitting unit 102, a second transmitting unit 104 and a receiving unit 106, wherein the receiving unit 106, the first transmitting unit 102 and the second transmitting unit 104 are disposed in the casing 100 side by side. The receiver 12 is electrically connected to the receiving unit 106 and the pulser 14 is electrically connected to the first transmitting unit 102, the second transmitting unit 104 and the receiver 12. Furthermore, the ultrasound probe 10 further comprises a matching layer 108, a backing layer 110 and a lens 112, wherein the matching layer 108 is disposed on the receiving unit 106, the first transmitting unit 102 and the second transmitting unit 104, the backing layer 110 and the matching layer 108 are disposed at opposite sides of the receiving unit 106, the first transmitting unit 102 and the second transmitting unit 104, and the lens 112 is disposed in the matching layer 108. The receiving unit 106 may also be used as a common diagnostic probe for scanning tissue structure. In this embodiment, the receiving unit 106 is used for receiving a reflective wave when detecting a shear wave. It should be noted that the ultrasound system 1 and the ultrasound probe 10 may be further equipped with other necessary circuits and components according to practical applications and those will not be depicted herein.

In this embodiment, the first transmitting unit 102 and the second transmitting unit 104 are located at opposite sides of the receiving unit 106. However, in another embodiment, the first transmitting unit 102 and the second transmitting unit 104 may be located at an identical side of the receiving unit 106 according to practical applications.

The receiving unit 106, the first transmitting unit 102 and the second transmitting unit 104 may be made of a piezoelectric material, wherein the piezoelectric material may be lead zirconate titanate (PZT), polyvinylidene (PVDF), Lithium Niobate (LiNbO3), PMNPT or other piezoelectric materials. Furthermore, the receiving unit 106 may essentially consist of a plurality of channels 1060, wherein the number of the channels 1060 may be 64, 128, 192, 256 or other values according to practical applications. It should be noted that a common coaxial cable has 134 cores. If the number of the channels 1060 of the receiving unit 106 is 128, the signal lines of the receiving unit 106, the first transmitting unit 102 and the second transmitting unit 104 may be integrated into one single coaxial cable.

In this embodiment, the first transmitting unit 102 is used for transmitting a first push beam and the second transmitting unit 104 is used for transmitting a second push beam, wherein the first push beam has a first transmitting frequency and the second push beam has a second transmitting frequency. Furthermore, the receiving unit 106 has a receiving frequency, wherein the receiving frequency is covered with the first transmitting frequency and the second transmitting frequency.

In general, an oscillation frequency of the ultrasound probe is related to a thickness of the piezoelectric material. The thickness of the piezoelectric material is equal to ½ wavelength and the relationship between wavelength, sound speed of material and center frequency is represented by the following equation 1.

$$\text{wavelength} = \text{sound speed of material/center frequency.} \quad \text{Equation 1:}$$

$$\text{center frequency} = (FL + FH/2). \quad \text{Equation 2:}$$

Where:
A Fast Fourier Transform (FFT) is performed on the echo pulse and the −6 dB levels of the rising edge (FL) and falling edge (FH) of the spectrum are summed then divided by two.

$$\text{Operating Bandwidth} = (FH - FL/\text{center frequency}) *100. \quad \text{Equation 3:}$$

Where:
A Fast Fourier Transform (FFT) is performed on the echo pulse. The difference from the −20 dB levels of the rising edge (FL) and falling edge (FH) of the spectrum are divided by the center frequency (FC) then multiplied by one hundred. It's usually more than 100% in the ultrasound transducer.

Accordingly, in the invention, a thickness t3 of the receiving unit 106 may be between a thickness t1 of the first transmitting unit 102 and a thickness t2 of the second transmitting unit 104, such that the receiving frequency of the receiving unit 106 may be between the first transmitting frequency of the first transmitting unit 102 and the second transmitting frequency of the second transmitting unit 104. For example, when the thickness t3 of the receiving unit 106 is ½ times the thickness t1 of the first transmitting unit 102 and the thickness t2 of the second transmitting unit 104 is ¼ times the thickness t1 of the first transmitting unit 102, the receiving frequency of the receiving unit 106 is two times the first transmitting frequency of the first transmitting unit 102 and the second transmitting frequency of the second transmitting unit 104 is four times the first transmitting frequency of the first transmitting unit 102. At this time, the wavelength of the matching layer 108 may be ¼, ⅛ and ¹⁄₁₆. Accordingly, a thickness t4 of the matching layer 108 of the invention may be uniform, wherein the thickness t4 of the matching layer 108 is corresponding to the first transmitting frequency, two times the first transmitting frequency (i.e. the receiving frequency), and four times the first transmitting frequency (i.e. the second transmitting frequency), i.e. equal to ¼ wavelength of the first transmitting frequency, ⅛ wavelength of the receiving frequency and ¹⁄₁₆ wavelength of the second transmitting frequency. In practical system design, the first transmitting frequency of the first transmitting unit 102 may be selected within a bandwidth range of 2-5 MHz with a center frequency of 3 MHz, the receiving frequency of the receiving unit 106 may receive a transmitting signal within bandwidth range of 3-9 MHz with a center frequency of 6 MHz, and the second transmitting frequency of the second transmitting unit 104 may be selected within a bandwidth range of 6-18 MHz with a center frequency of 12 MHz. However, the invention is not limited to the aforesaid embodiments.

It should be noted that if the relationship between the first transmitting frequency of the first transmitting unit 102, the receiving frequency of the receiving unit 106 and the second transmitting frequency of the second transmitting unit 104 is not a multiple of 2, the thickness of the matching layer 108 may be various, so as to be corresponding to the first transmitting frequency of the first transmitting unit 102, the receiving frequency of the receiving unit 106 and the second transmitting frequency of the second transmitting unit 104.

When the ultrasound system 1 of the invention is used to perform ultrasound scanning, the pulser 14 is used for triggering the first transmitting unit 102 and the second transmitting unit 104 to selectively transmit the first push beam and the second push beam and the receiving unit 106 is used for selectively receiving a reflective wave (i.e. shear wave) of the first push beam and the second push beam.

For example, when a doctor wants to use the ultrasound system 1 of the invention to scan a tissue of liver, breast or the like, he/she can operate the pulser 14 to trigger the first transmitting unit 102 to transmit a first push beam with a first frequency (e.g. 3 MHz, low frequency) and then the receiving unit 106 receives a reflective wave of the first push beam. At this time, the pulser 14 will trigger the receiver 12 to receive the reflective wave of the first push beam from the receiving unit 106. Then, a backend control circuit (not shown) processes the reflective wave of the first push beam and generates an image. Similarly, when the doctor wants to use the ultrasound system 1 of the invention to scan a tissue of a small area, he/she can operate the pulser 14 to trigger the second transmitting unit 104 to transmit a second push beam with a second frequency (e.g. 12 MHz, high frequency) and then the receiving unit 106 receives a reflective wave of the second push beam. At this time, the pulser 14 will trigger the receiver 12 to receive the reflective wave of the second push beam from the receiving unit 106. Then, the backend control circuit (not shown) processes the reflective wave of the second push beam and generates an image.

As mentioned in the above, the invention integrates the two transmitting units and the receiving unit into the ultrasound probe, wherein the two transmitting units can transmit two push beams with different frequencies. Accordingly, the ultrasound probe of the invention can selectively transmit a push beam with low frequency to scan a tissue of liver, breast or the like or transmit a push beam with high frequency to scan a tissue of a small area. In other words, the ultrasound probe of the invention can perform ultrasound scanning for tissues located at different distances. Therefore, the invention is very convenient in use.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An ultrasound probe comprising:
    a casing;
    a first transmitting unit for transmitting a first push beam, the first push beam having a first transmitting frequency;
    a second transmitting unit for transmitting a second push beam, the second push beam having a second transmitting frequency, the first transmitting frequency being different from the second transmitting frequency;
    a receiving unit having a receiving frequency, the receiving unit being used for selectively receiving a reflective wave of the first push beam and the second push beam, the receiving frequency being covered with the first transmitting frequency and the second transmitting frequency, the receiving unit, the first transmitting unit and the second transmitting unit being disposed in the casing side by side; and
    a matching layer disposed on the receiving unit, the first transmitting unit and the second transmitting unit;
    wherein the receiving frequency is two times the first transmitting frequency and the second transmitting frequency is four times the first transmitting frequency, such that a thickness of the receiving unit is ½ times a thickness of the first transmitting unit, a thickness of the second transmitting unit is ¼ times the thickness of the first transmitting unit, and a thickness of the matching layer is uniform.

2. The ultrasound probe of claim 1, wherein the first transmitting unit and the second transmitting unit are located at opposite sides of the receiving unit.

3. The ultrasound probe of claim 1, wherein a thickness of the receiving unit is between a thickness of the first transmitting unit and a thickness of the second transmitting unit.

4. The ultrasound probe of claim 1, wherein the receiving unit, the first transmitting unit and the second transmitting unit are made of a piezoelectric material.

5. The ultrasound probe of claim 1, wherein the receiving unit essentially consists of a plurality of channels.

6. The ultrasound probe of claim 1, further comprising a backing layer, the backing layer and the matching layer being disposed at opposite sides of the receiving unit, the first transmitting unit and the second transmitting unit.

7. The ultrasound probe of claim 1, further comprising a lens disposed on the matching layer.

8. An ultrasound system comprising:
    an ultrasound probe comprising:
        a casing;
        a first transmitting unit for transmitting a first push beam, the first push beam having a first transmitting frequency;
        a second transmitting unit for transmitting a second push beam, the second push beam having a second transmitting frequency, the first transmitting frequency being different from the second transmitting frequency;
        a receiving unit having a receiving frequency, the receiving frequency being covered with the first transmitting frequency and the second transmitting frequency, the receiving unit, the first transmitting unit and the second transmitting unit being disposed in the casing side by side; and
        a matching layer disposed on the receiving unit, the first transmitting unit and the second transmitting unit;
        wherein the receiving frequency is two times the first transmitting frequency and the second transmitting frequency is four times the first transmitting frequency, such that a thickness of the receiving unit is ½ times a thickness of the first transmitting unit, a thickness of the second transmitting unit is ¼ times the thickness of the first transmitting unit, and a thickness of the matching layer is uniform;
    a receiver electrically connected to the receiving unit; and
    a pulser electrically connected to the first transmitting unit, the second transmitting unit and the receiver, the pulser being used for triggering the first transmitting unit and the second transmitting unit to selectively transmit the first push beam and the second push beam.

9. The ultrasound system of claim 8, wherein the first transmitting unit and the second transmitting unit are located at opposite sides of the receiving unit.

10. The ultrasound system of claim 8, wherein a thickness of the receiving unit is between a thickness of the first transmitting unit and a thickness of the second transmitting unit.

11. The ultrasound system of claim 8, wherein the receiving unit, the first transmitting unit and the second transmitting unit are made of a piezoelectric material.

12. The ultrasound system of claim 8, wherein the receiving unit essentially consists of a plurality of channels.

13. The ultrasound system of claim 8, wherein the ultrasound probe further comprises a backing layer, and the backing layer and the matching layer are disposed at opposite sides of the receiving unit, the first transmitting unit and the second transmitting unit.

14. The ultrasound system of claim 8, wherein the ultrasound probe further comprises a lens disposed on the matching layer.

* * * * *